US009283330B2

(12) United States Patent  (10) Patent No.: US 9,283,330 B2
Iwase et al.  (45) Date of Patent: Mar. 15, 2016

(54) INJECTION NEEDLE ASSEMBLY AND DRUG INJECTION APPARATUS

(75) Inventors: Yoichiro Iwase, Ashigarakami-gun (JP); Takayuki Yokota, Nakakoma-gun (JP); Yoshinori Hishikawa, Nakakoma-gun (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 383 days.

(21) Appl. No.: 13/579,805

(22) PCT Filed: Feb. 10, 2011

(86) PCT No.: PCT/JP2011/052872
§ 371 (c)(1),
(2), (4) Date: Aug. 17, 2012

(87) PCT Pub. No.: WO2011/111468
PCT Pub. Date: Sep. 15, 2011

(65) Prior Publication Data
US 2013/0006179 A1   Jan. 3, 2013

(30) Foreign Application Priority Data
Mar. 10, 2010   (JP) .................................. 2010-053831

(51) Int. Cl.
*A61M 5/32*   (2006.01)
*A61M 5/46*   (2006.01)
(Continued)

(52) U.S. Cl.
CPC ............ *A61M 5/3287* (2013.01); *A61B 17/205* (2013.01); *A61M 5/46* (2013.01); *A61B 2019/302* (2013.01); *A61M 5/002* (2013.01); *A61M 5/344* (2013.01)

(58) Field of Classification Search
CPC ....... A61M 5/34; A61M 5/344; A61M 5/345; A61M 5/46; A61M 2005/3267; A61M 2005/3143; A61B 2019/303; A61B 2019/306
USPC ......................................................... 604/117
See application file for complete search history.

(56) References Cited

U.S. PATENT DOCUMENTS 5,688,241 A  * 11/1997  Asbaghi ........................ 604/110
5,769,826 A  *  6/1998  Johnson et al. ............... 604/195
(Continued)

FOREIGN PATENT DOCUMENTS

JP   2000-37456 A   2/2000
JP   2001-137343 A   5/2001
(Continued)

OTHER PUBLICATIONS

International Search Report (PCT/ISA/210) issued on Mar. 8, 2011, by the Japanese Patent Office as the International Searching Authority for International Application No. PCT/JP2011/052872.
(Continued)

*Primary Examiner* — Nathan R Price
*Assistant Examiner* — Weng Lee
(74) *Attorney, Agent, or Firm* — Buchanan Ingersoll & Rooney PC (57) ABSTRACT

An injection needle assembly includes a needle tube having a needle tip to be stuck into a skin, a first member, a second member, an adjustment portion, and a pressing force restricting member. The first member holds the needle tube and the second member holds the first member movably toward the axial direction of the needle tube. A discharge portion of the syringe is fitted into this second member. The adjustment portion is provided at the periphery of the needle tube and includes a needle protrusion surface which abuts the skin in a case in which the needle tube is stuck to the living body. The pressing force restricting member is arranged between the first member and the second member, and restricts the pressing force added from the first member to the skin.

20 Claims, 6 Drawing Sheets

(51) Int. Cl.
*A61B 17/20* (2006.01)
*A61M 5/00* (2006.01)
*A61M 5/34* (2006.01)
*A61B 19/00* (2006.01)

(56) References Cited

U.S. PATENT DOCUMENTS

| | | | |
|---|---|---|---|
| 6,547,764 B2 * | 4/2003 | Larsen et al. | 604/192 |
| 7,247,149 B2 * | 7/2007 | Beyerlein | 604/117 |
| 7,556,615 B2 * | 7/2009 | Pettis et al. | 604/117 |
| 7,691,083 B2 * | 4/2010 | Botich et al. | 604/110 |
| 7,981,081 B2 * | 7/2011 | Marsh et al. | 604/117 |
| 2002/0004648 A1 * | 1/2002 | Larsen et al. | 604/195 |
| 2003/0050602 A1 * | 3/2003 | Pettis et al. | 604/117 |
| 2003/0078546 A1 * | 4/2003 | Jensen | 604/232 |
| 2004/0092872 A1 * | 5/2004 | Botich et al. | 604/110 |
| 2005/0000514 A1 * | 1/2005 | Sullivan et al. | 128/200.24 |
| 2006/0229570 A1 * | 10/2006 | Lovell et al. | 604/218 |
| 2007/0118077 A1 * | 5/2007 | Clarke et al. | 604/117 |
| 2007/0129686 A1 | 6/2007 | Daily et al. | |
| 2008/0033395 A1 | 2/2008 | Alchas | |

FOREIGN PATENT DOCUMENTS

| | | |
|---|---|---|
| JP | 2005-527249 A | 9/2005 |
| JP | 2007-505677 A | 3/2007 |
| WF | WO 03/022330 A2 | 3/2003 |
| WO | 99/33504 A1 | 7/1999 |
| WO | 2005/079441 A2 | 9/2005 |

OTHER PUBLICATIONS

Extended Search Report issued on Apr. 4, 2014, by the European Patent Office in corresponding European Patent Application No. 11753130.1. (6 pages).

* cited by examiner

INJECTION NEEDLE ASSEMBLY AND DRUG INJECTION APPARATUS

TECHNICAL FIELD

The present invention relates to an injection needle assembly and a medicine injection apparatus used for sticking a needle tip from the surface of a skin and for injecting medicine into an upper layer region of the skin.

BACKGROUND ART

In recent years, there have been reported infections of avian influenza to humans, and there are concerns about a lot of damage caused by a large epidemic (pandemic) of infections from human to human. Consequently, prepandemic vaccines which have the possibility of being effective against the avian influenza are being stockpiled all over the world. Also, in order to administer the prepandemic vaccines to many people, there have been carried out examinations for enlarging the manufacturing quantities of the vaccines.

The skin is composed of three portions: the epidermis, the dermis, and the subcutaneous tissue. The epidermis is a layer ranging between approximately 50 μm and 200 μm from the surface of the skin, and the dermis is a layer ranging between approximately 1.5 mm and 3.5 mm continuous from the epidermis. An influenza vaccine is ordinarily administered in a hypodermic or intramuscular manner, and therefore, it is injected into a lower layer portion of the skin or a portion deeper than the lower layer portion.

On the other hand, there was reported an article that an immune obtaining response equivalent to a hypodemic administration and a muscle administration can be obtained by administering influenza vaccine in a situation of making an upper layer region of a skin where a lot of immunocompetent cells exist as a target region even if the applied dose is reduced. Therefore, it is possible to reduce the applied dose by administering the avian influenza vaccine into the upper layer region of the skin, so that there is a possibility that the avian influenza vaccine can be administered to more people. Note that the wording "upper layer region of the skin" indicates "epidermis" and "dermis" within the skin.

As administration methods of medicine to an upper layer region of a skin, there have been reported methods using a single needle, multiple needles, a patch, gas and the like. Then, when taking stability, reliability and manufacturing cost of the administration into account, the method using a single needle is the most suitable as the administration method to the upper layer region of the skin. As this method of administering vaccine to an upper layer region of a skin by using a single needle, there has been known a Mantoux method from old times. The Mantoux method is a method in which medicine of around 100 μL is administered by inserting a needle having a needle tip of short bevel with a size of generally 26 to 27 gauge by an amount of around 2 mm to 5 mm from an oblique direction of around 10° to 15° with respect to the skin.

However, in the Mantoux method, the procedure thereof is difficult, and the procedure is left up to the skill of a doctor who carries out the injection. In particular, there is a possibility that the infant may move at the time of administration, so that it is difficult to administer influenza vaccine by the Mantoux method. Therefore, development of a device is required which can easily administer vaccine to the upper layer region of the skin.

In Patent Document 1, there is described an injection apparatus in which a limiter having a skin contact surface is connected to a needle hub of an injector. The limiter of the injection apparatus described in this Patent Document 1 is formed in a tubular shape covering the periphery of the needle tube and includes a skin contact surface from which the injection needle protrudes. This limiter restricts the length of the injection needle (protrusion length) protruding from the skin contact surface to the range of 0.5 mm to 3.0 mm and the medicine injected from the injection needle is made to be administered into the inside of the skin.

Also, In Patent Document 2, there is described an apparatus relating to a sticking adjuster for an injection needle and an injection needle assembly provided with that adjuster which prevent the injection needle from being stuck more deeply than an aimed depth. Within the sticking adjusters for injection needles disclosed in this Patent Document 2, there exists a sticking adjuster for an injection needle which closely-contacts with the periphery of the injection needle and which includes a skin contact surface.

PRIOR-ART DOCUMENT

Patent Document

Patent Document 1: Japanese unexamined patent publication No. 2001-137343
Patent Document 2: Japanese unexamined patent publication No. 2000-37456

DISCLOSURE OF THE INVENTION

Problem to be Solved by the Invention

However, according to the technology disclosed in the Patent Document 1, 2, when, for example, the thickness of the upper layer region of the skin in the deltoid periphery is thinner than that of the average value and the pressing force of the injector to the skin is such a strong pressing force exceeding 20N, it happens that the skin abutting the skin contact surface becomes thin and the needle tube will reach the subcutaneous region. As a result thereof, there occurred such a problem that it is not possible to administer medicine (vaccine) to the upper layer region of the skin. As mentioned above, the antigen level of the medicine in case of making the upper layer region of the skin as a target region is fewer than the antigen level of the medicine in case of making the subcutaneous region as a target region. Therefore, when it happens that the needle tube reaches the subcutaneous region by a strong pressing force, it happens that there cannot be obtained a desired immune obtaining response.

In order to prevent the needle tube from reaching the subcutaneous region, for example, a method is conceivable in which the pressing force added to the skin is reduced by making the skin contact surface larger. However, when making the skin contact surface larger, there occurred such a problem that it becomes easy for the skin at the periphery of the needle tube to bend and it becomes difficult for the needle tube to be stuck into the skin caused by the fact that the distance from the peripheral edge of the skin contact surface to the needle tube becomes longer.

The present invention was invented in view of such a situation and has an object to provide an injection needle assembly and a medicine injection apparatus in which it is possible to position the needle tube at the upper layer region of the skin reliably even in a case in which the pressing force to the skin is strong.

Means for Solving the Problem

In order to solve the abovementioned problem and to achieve an object of the present invention, an injection needle assembly of the present invention is provided with a needle tube having a needle tip to be stuck into a skin, a first member, a second member, an adjustment portion, and a pressing force restricting member. The first member holds the needle tube and the second member holds the first member movably in the axial direction of the needle tube. A discharge portion of a syringe is fitted into this second member. The adjustment portion is provided at the periphery of the needle tube and includes a needle protrusion surface which abuts the skin in case of sticking the needle tube into a living body. The pressing force restricting member is arranged between the first member and the second member and restricts pressing force added from the first member to the skin.

Also, a medicine injection apparatus of the present invention is provided with a syringe including a discharge portion, a needle tube having a needle tip to be stuck into a skin, a first member, a second member, an adjustment portion, and a pressing force restricting member. The first member holds the needle tube and the second member holds the first member movably in the axial direction of the needle tube. The discharge portion of the syringe is fitted into this second member. The adjustment portion is provided at the periphery of the needle tube and includes a needle protrusion surface which abuts the skin in case of sticking the needle tube into a living body. The pressing force restricting member is arranged between the first member and the second member and restricts pressing force added from the first member to the skin.

In the injection needle assembly and the medicine injection apparatus of the present invention, the first member is held by the second member movably in the axial direction of the needle tube, and the pressing force added from that first member to the skin is restricted by the pressing force restricting member. Thus, it is possible to restrict the pressing force to the skin by the needle protrusion surface of the adjustment portion provided at the periphery of the needle tube. As a result thereof, even in a case in which the pressing force to the skin is strong, it is possible to prevent the skin abutting the needle protrusion surface from becoming thin and to position the needle tube reliably at the upper layer region of the skin.

Effect of the Invention

According to the medicine injection apparatus and the injection needle assembly of the present invention, even in a case in which the pressing force to the skin is strong, it is possible to prevent the skin abutting the needle protrusion surface from becoming thin and to position the needle tube reliably in the upper layer region of the skin.

MODE FOR CARRYING OUT THE INVENTION

Hereinafter, there will be explained embodiments for carrying out the injection needle assembly and the medicine injection apparatus of the present invention with reference to the drawings. Note in each drawing that common features and members are denoted by the same reference numerals.

1. First Exemplified Embodiment

Medicine Injection Apparatus

First, there will be explained a first embodiment of a medicine injection apparatus and an injection needle assembly of the present invention with reference to FIG. 1 and FIG. 2.

Figure 1:
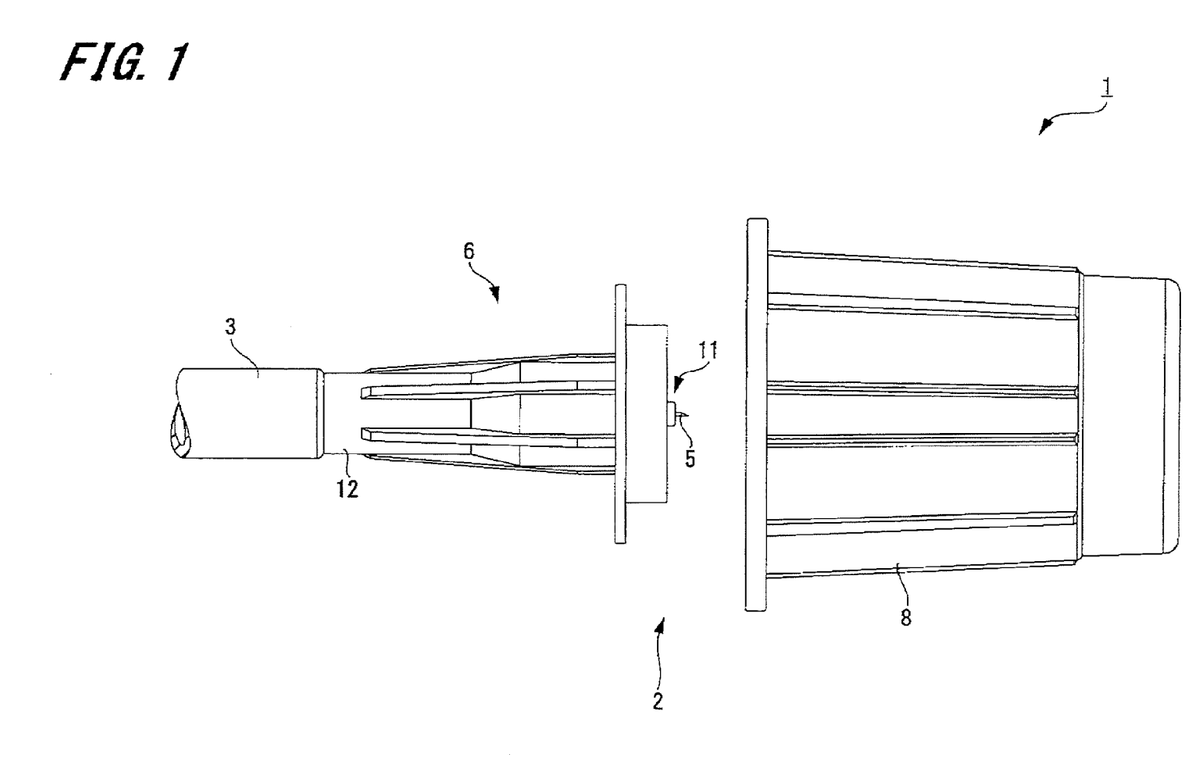
FIG. 1 is a side view of a first embodiment of a medicine injection apparatus of the present invention.
Figure 2:
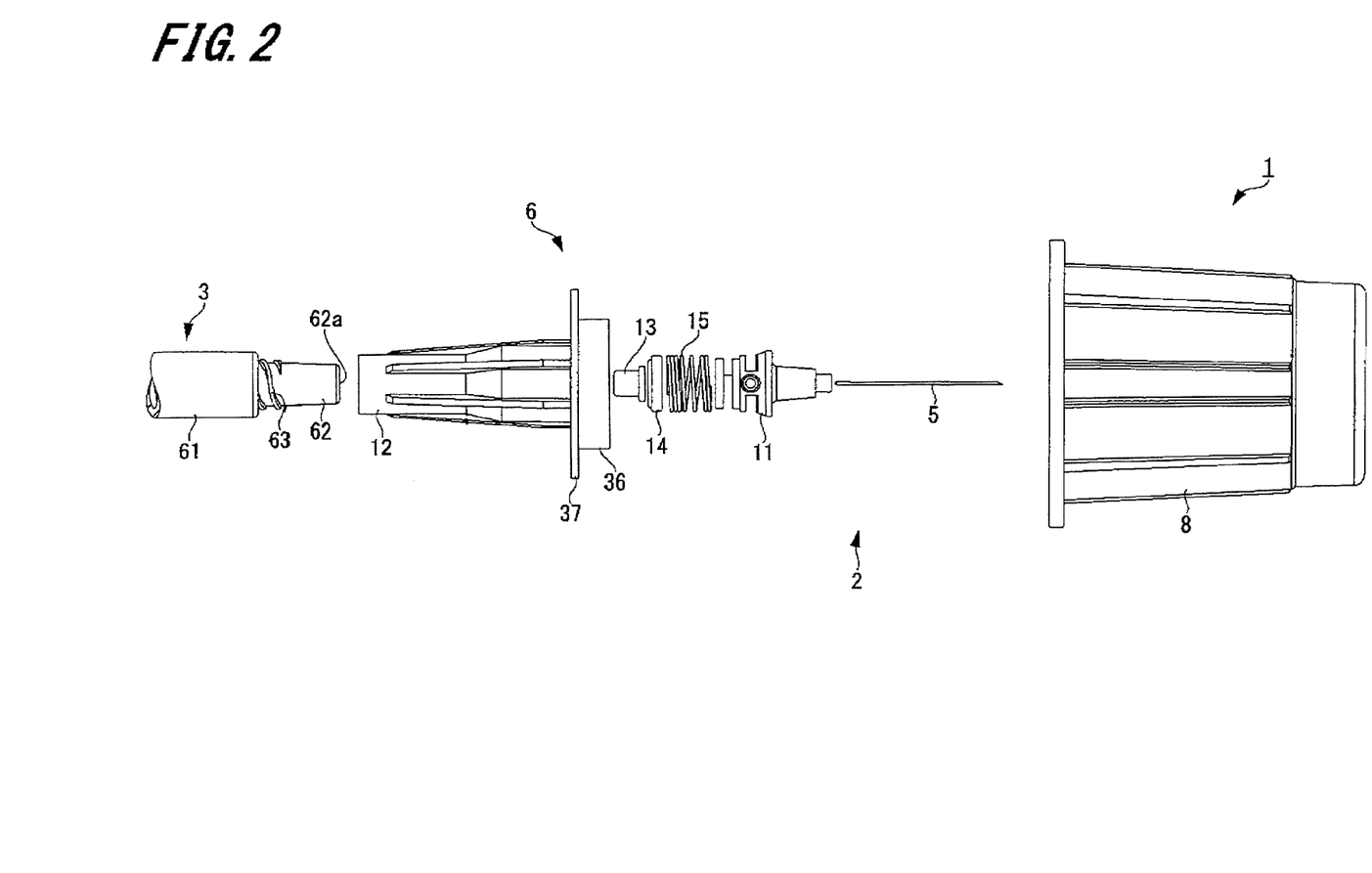
FIG. 2 is an exploded view of the first embodiment of the medicine injection apparatus of the present invention.

FIG. 1 is a side view of a first embodiment of a medicine injection apparatus. FIG. 2 is an exploded view of the first embodiment of the medicine injection apparatus.

A medicine injection apparatus 1 is used in case of sticking a needle tip from the surface of a skin and injecting medicine into the upper layer region of the skin. This medicine injection apparatus 1 includes an injection needle assembly 2 and a syringe 3 to which this injection needle assembly 2 is connected detachably.

As shown in FIG. 1, the injection needle assembly 2 includes a hollow needle tube 5 having a needle hole, a needle hub 6 to which this needle tube 5 is to be fixed, and a cap 8 detachably attached to the needle hub 6. The needle hub 6 is, as shown in FIG. 2, constituted by a first member 11 which holds the needle tube 5, a second member 12 into which a discharge portion 62 to be described later of the syringe 3 is to be fitted, a communication member 13, a locking member 14, and a pressing force restricting member 15.

Figure 3:
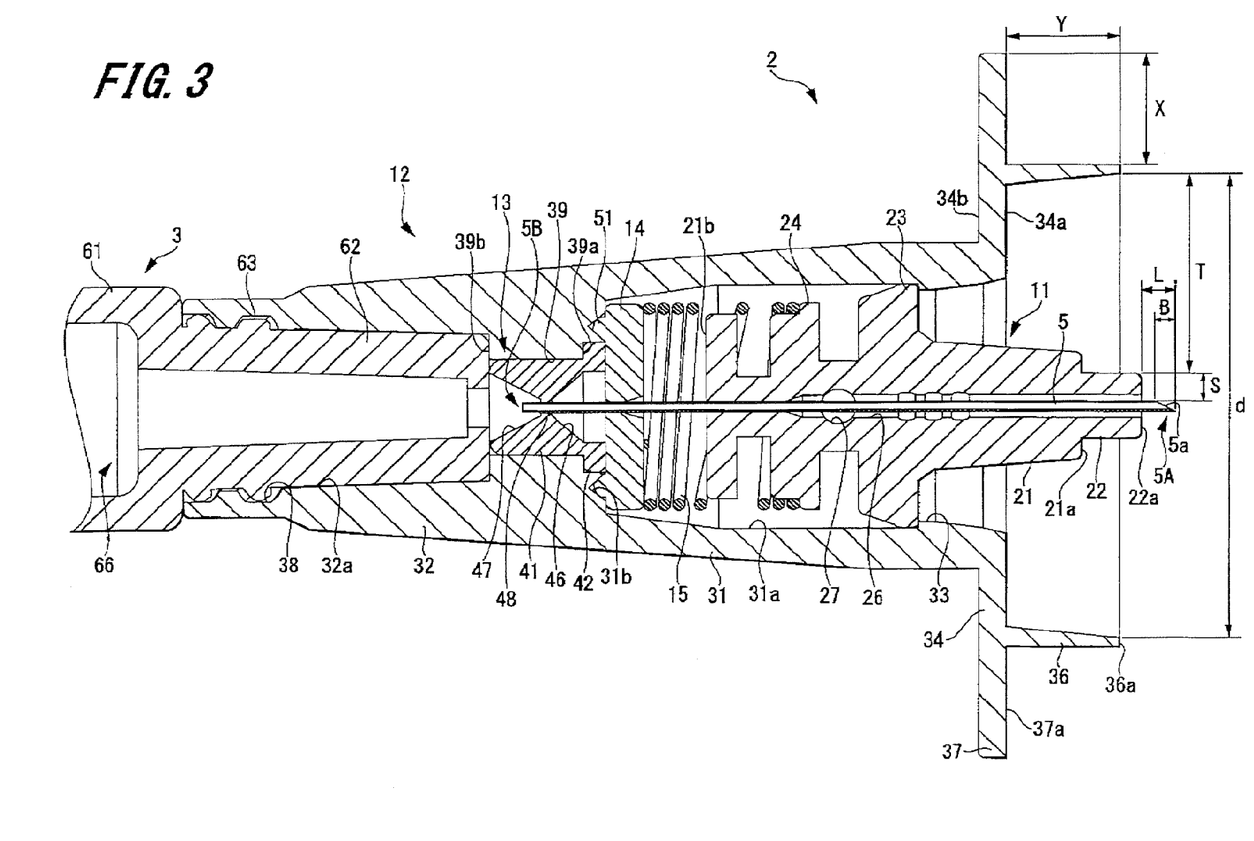
FIG. 3 is a cross-sectional view of the first embodiment of the medicine injection apparatus of the present invention.
Figure 4:
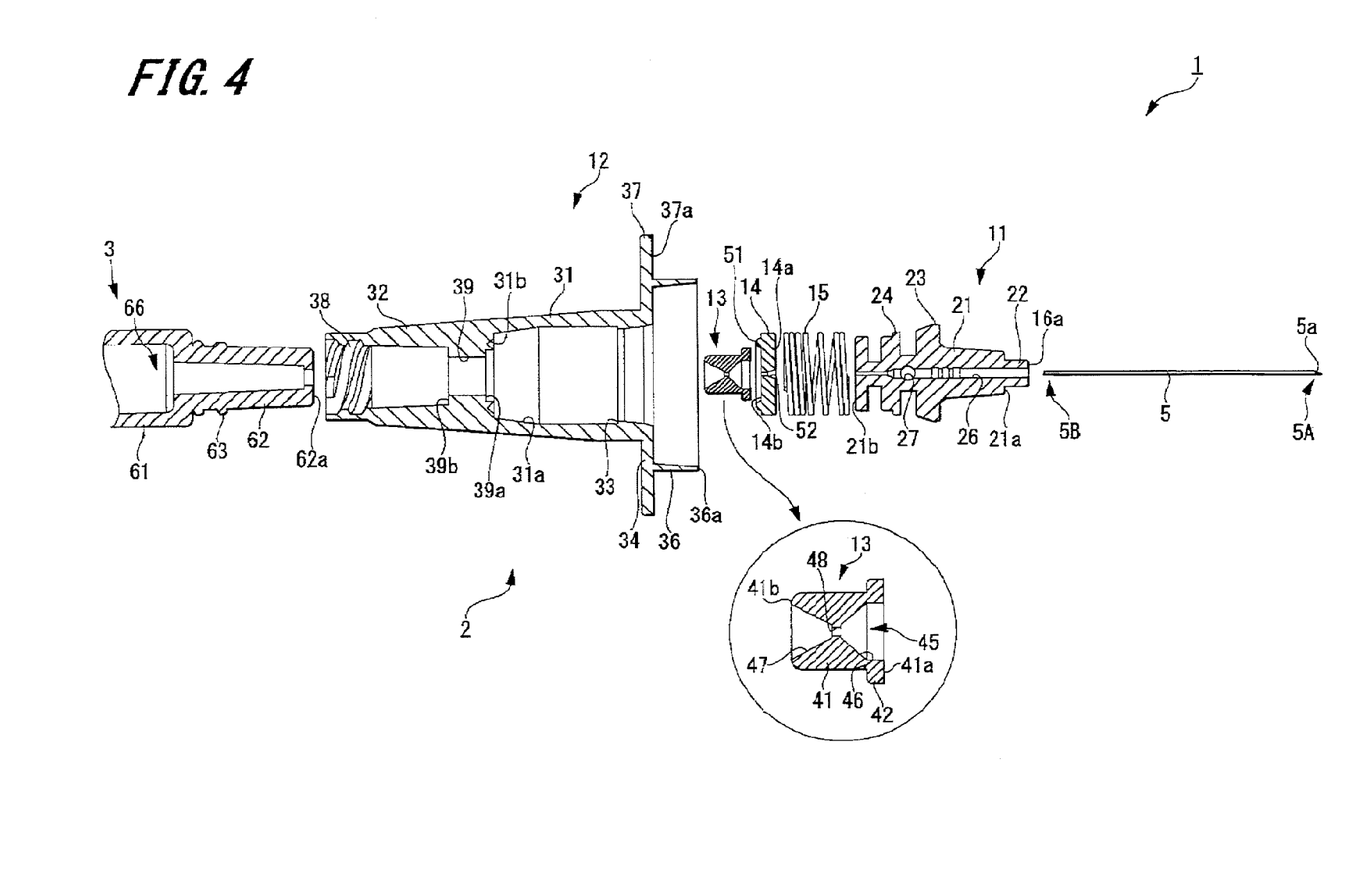
FIG. 4 is a cross-sectional view showing, in an exploded form, the first embodiment of the medicine injection apparatus of the present invention.

Next, there will be explained the injection needle assembly 2 and the syringe 3 with reference to FIG. 3 and FIG. 4. FIG. 3 is a cross-sectional view of the medicine injection apparatus 1. FIG. 4 is a cross-sectional view showing, in an exploded form, the medicine injection apparatus 1.

[Injection Needle Assembly]

For the needle tube 5 of the injection needle assembly 2, there is used a tube having a size of 26 to 33 gauge (0.2 mm to 0.45 mm outer-diameter) according to the ISO standard of a needle tube for medication (ISO9626:1991/Amd. 1:2001(E)), and preferably a tube having a size of 30 to 33 gauge.

One end of the needle tube 5 is provided with a needle tip 5A having a bevel 5a. Hereafter, the other end of the needle tube 5 lying on the opposite side of the needle tip 5A is referred to as the "proximal end 5B". It is enough if the length of the bevel 5a along the axial direction of the needle tube 5 (hereinafter, the length is referred to as "bevel length B") is equal to or less than 1.4 mm, which is the minimum thickness of the skin upper layer region (for adults) to be described later and also, it is enough if the bevel length B is equal to or more than approximately 0.5 mm, which is a bevel length when a short bevel is formed on a 33 gauge needle tube. In other words, it is preferable for the bevel length B to be set in the range of 0.5 mm to 1.4 mm.

Further, it is more preferable for the bevel length B to be equal or less than 0.9 mm, which is the minimum thickness of the skin upper layer region (for infants), that is, it is more preferable for the bevel length B to be in the range of 0.5 mm to 0.9 mm. Note that the term "short bevel" means a bevel which is formed with an angle of 18° to 25° with respect to the longitudinal direction of the needle and which is generically used for injection needles.

For the material of the needle tube 5, there can be cited, for example, stainless steel, but it is not limited by this material and it is possible to use aluminum, aluminum alloys, titanium, titanium alloys and other metals. Also, for the needle tube 5, it is possible to use not only a straight needle but also a tapered needle which is tapered at least for a portion thereof. For the tapered needle, it is enough if there is employed a needle in which the proximal portion thereof has a larger diameter compared with that of the distal portion and a tapered structure is applied to an intermediate portion thereof. Also, the cross-sectional shape of the needle tube 5 is not limited to a circle but may be a polygon such as a triangle.

Next, there will be explained the needle hub 6. The first member 11 and the second member 12 of the needle hub 6 are formed as separate members. The second member 12 holds the first member 11 in a state of holding the needle tube 5 movably in the axial direction of the needle tube 5. For the material of these first member 11 and second member 12, there can be cited synthetic resin (plastic) such as polycarbonate, polypropylene, polyethylene and the like.

The first member 11 includes a base portion 21 and an adjustment portion 22. The base portion 21 is formed approximately in a cylindrical shape and has end surfaces 21*a* and 21*b* perpendicular to the axial direction of the base portion 21. Also, on the outer circumferential surface of the base portion 21, there are provided a first engagement portion 23 which engages with a stopper portion 33, which will be described later, of the second member 12 and a second engagement portion 24 which engages with one end of the pressing force restricting member 15. The adjustment portion 22 is provided at a central portion of the end surface 21*a* of the base portion 21 and is composed of a cylindrical projected portion projecting in the axial direction of the base portion 21. The axis of this adjustment portion 22 coincides with the axis of the base portion 21.

For the axis of the base portion 21 and the adjustment portion 22, there is provided a through-hole 26 through which the needle tube 5 passes (see FIG. 4). Then, for the base portion 21, there is provided an injection hole 27 for injecting an adhesive agent (not shown) into the through-hole 26. This injection hole 27 opens on the outer peripheral surface of the base portion 21 and communicates with the through-hole 26. More specifically, by virtue of the adhesive agent injected from the injection hole 27 into the through-hole 26, the needle tube 5 is firmly attached to the base portion 21.

The proximal end 5B side of the needle tube 5 protrudes from the end surface 21*b* of the base portion 21. The base portion 21 is inserted into the inside of the second member 12 from the end surface 21*b* side and the proximal end 5B side of the needle tube 5 is inserted into an insertion hole 45, which will be described later, of the communication member 13.

An end surface of the adjustment portion 22 constitutes a needle protrusion surface 22*a* from which the needle tip 5A side of the needle tube 5 protrudes outward. The needle protrusion surface 22*a* is formed as a flat surface orthogonal to the axial direction of the needle tube 5. When the needle tube 5 is stuck into the skin upper layer region, this needle protrusion surface 22*a* contacts the surface of the skin and restricts the sticking depth. In other words, the depth to be stuck into the skin upper layer region by the needle tube 5 is determined by the length of the needle tube 5 protruding from the needle protrusion surface 22*a* (Hereinafter, this length will be referred to as "protrusion length L".) (see FIG. 3).

The thickness of the skin upper layer region corresponds to the depth from the surface of the skin to the dermis layer and roughly, it is in the range of 0.5 mm to 3.0 mm. Therefore, it is possible for the protrusion length L of the needle tube 5 to be set in the range of 0.5 mm to 3.0 mm.

Meanwhile, vaccines are generally administered into an upper arm region and in case of administration thereof into a skin upper layer region, it is preferable to select a thick-skinned shoulder peripheral region, in particular, a deltoid region. In view of this, the thickness of the skin upper layer region at the deltoid muscle was measured with respect to 19 infants and 31 adults. This measurement was carried out by imaging the skin upper layer region having high ultrasonic reflectance by using an ultrasonic measuring apparatus (NP60R-UBM, a high-resolution echo system for small animals, produced by NEPA GENE CO., LTD.). Note that the measurement value showed log normal distribution and therefore, the range of MEAN±2SD was found according to the geometric mean.

As a result thereof, the thickness of the skin upper layer region at the deltoid muscles of infants was found to be 0.9 mm to 1.6 mm. Also, the thickness of the skin upper layer region at the deltoid muscles of adults was found to be 1.4 mm to 2.6 mm in a distal region, to be 1.4 mm to 2.5 mm in a central region and to be 1.5 mm to 2.5 mm in a proximal region. From the matters above, it was confirmed that the thickness of the skin upper layer region at the deltoid muscle is 0.9 mm or more for infants and 1.4 mm or more for adults. Therefore, in the injection into the skin upper layer region at the deltoid muscle, it is preferable for the protrusion length L of the needle tube 5 to be set in the range of 0.9 mm to 1.4 mm.

By setting the protrusion length L in this manner, it is possible to position the bevel 5*a* of the needle tip 5A in the skin upper layer region. As the result thereof, the needle hole (liquid medicine discharge port) opened at the bevel 5*a* is to be located in the skin upper layer region regardless of the position thereof in the bevel 5*a*. Note that if the needle tip 5A is stuck into a position deeper than the skin upper layer region even in a case in which the liquid medicine discharge port is located in the skin upper layer region, the liquid medicine will flow into the subcutaneous tissue, so that the fact that the bevel 5*a* is reliably located within the skin upper layer region is important.

Note that in case of a needle tube thicker than 26 gauge, it is difficult to set the bevel length B to be 1.0 mm or less. Therefore, in order to set the protrusion length L of the needle tube 5 to be within the preferable range (0.9 mm to 1.4 mm), it is preferable to use a needle tube thinner than 26 gauge.

The needle protrusion surface 22*a* is formed such that the distance S from its peripheral edge to the outer peripheral surface of the needle tube 5 becomes 1.4 mm or less and is preferably formed within the range of 0.3 mm to 1.4 mm. This distance S from the outer peripheral edge of the needle protrusion surface 22*a* to the outer peripheral surface of the needle tube 5 is set in consideration of the fact that a pressure is exerted on a water blister formed by injecting the medicine into the skin upper layer region. In other words, the needle protrusion surface 22*a* is set to be sufficiently smaller than the water blister to be formed in the skin upper layer region and to be a size which does not block the formation of the water blister. As a result thereof, even when the needle protrusion surface 22a presses the skin in the surroundings of the needle tube 5, it is possible to prevent the injected medicine from leaking.

Next, there will be explained the second member 12. The second member 12 is formed to be approximately in a cylindrical shape. One end portion in the axial direction of this second member 12 is constituted as an insertion portion 31 into which the base portion 21 of the first member 11 is to be inserted and the other end portion is constituted as a fitting portion 32 into which the discharge portion 62 of the syringe 3 is to be fitted. A cylinder hole 31a of the insertion portion 31 is set to have a size corresponding to that of the base portion 21 of the first member 11. Also, on the inner circumferential surface of the insertion portion 31, there is provided the stopper portion 33 which is engaged with the first engagement portion 23 of the first member 11.

On the outer circumferential surface of the insertion portion 31, there is provided a connection piece 34. This connection piece 34 is formed as a ring-shaped flange projecting toward the radial direction of the insertion portion 31 and includes flat surfaces 34a, 34b facing each other in the axial direction of the insertion portion 31. On the flat surface 34a of the connection piece 34, there is provided a stabilization portion 36. Also, the region on the distal side from the stabilization portion 36 of the connection piece 34 is constituted to be a guide portion 37. This guide portion 37 is fitted with the cap 8 detachably.

The stabilization portion 36 is formed in a cylindrical shape and protrudes from the flat surface 34a of the connection piece 34. The adjustment portion 22 is disposed in a cylinder hole of the stabilization portion 36. In other words, the stabilization portion 36 is formed in a cylindrical shape which surrounds the adjustment portion 22 through which the needle tube 5 passes and is provided by being apart from the needle tip 5A of the needle tube 5 toward the radial direction.

As shown in FIG. 3, the end surface 36a of the stabilization portion 36 is located on the side of the proximal end 5D of the needle tube 5 compared with the needle protrusion surface 22a of the adjustment portion 22. When the needle tip 5A of the needle tube 5 is stuck into a living body, the needle protrusion surface 22a first comes into contact with the surface of the skin and thereafter, the end surface 36a of the stabilization portion 36 touches the surface of the skin. At that time, by the fact that the end surface 36a of the stabilization portion 36 contacts with the skin, the medicine injection apparatus 1 is stabilized and it is possible to keep the needle tube 5 in a posture of being approximately perpendicular to the skin.

Note that even if the end surface 36a of the stabilization portion 36 is made to locate on the same plane as the needle protrusion surface 22a and also, even if it is made to locate on the side of the needle tip 5A of the needle tube 5 compared with the needle protrusion surface 22a, it is possible to maintain the needle tube 5 in a posture approximately perpendicular to the skin. When taking the bulging of the skin into account on an occasion of pressing the stabilization portion 36 toward the skin, it is preferable for the distance between the end surface 36a of the stabilization portion 36 and the needle protrusion surface 22a along the axial direction to be set to be 1.3 mm or less.

Also, the inner diameter d of the stabilization portion 36 is set to be equal to or greater than the diameter of the water blister which is formed in the skin. Specifically, the distance T from the inner wall surface of the stabilization portion 36 to the outer peripheral edge of the needle protrusion surface 22a is set so as to fall into a range of 4 mm to 15 mm. Thus, a pressure is never exerted on the water blister from the inner wall surface of the stabilization portion 36 and it is possible to prevent the water blister formation from being disturbed.

If the distance T from the inner wall surface of the stabilization portion 36 to the peripheral edge of the needle protrusion surface 22a is selected to be 4 mm or more, there is no upper limit for the distance thereof. However, when increasing the distance T, the outside diameter of the stabilization portion 36 becomes larger, so that in case of sticking the needle tube 5 into a slender arm such as the arm of an infant, it becomes difficult to bring the whole portion of the end surface 36a of the stabilization portion 36 into contact with the skin. Therefore, taking the slenderness of an infant's arm into account, it is preferable to define the distance T to be 15 mm for the maximum value.

If the distance S from the peripheral edge of the needle protrusion surface 22a to the outer peripheral surface of the needle tube 5 is 0.3 mm or more, the adjustment portion 22 will not enter into the skin. Therefore, taking into account the distance T (4 mm or more) from the inner wall surface of the stabilization portion 36 to the peripheral edge of the needle protrusion surface 22a and the diameter (approximately 0.3 mm) of the needle protrusion surface 22a, it is possible to set the inner diameter d of the stabilization portion 36 to be 9 mm or more.

Note that the shape of the stabilization portion 36 is not limited to a cylindrical shape and it is allowed, for example, to form the shape as an angled tubular shape such as a quadratic prism, a hexagonal prism or the like having a tubular hole in the center thereof.

The guide portion 37 has a contact surface 37a to be brought into contact with the skin. The contact surface 37a is a portion of the flat surface 34a of the connection piece 34 and is a flat surface approximately in parallel with the end surface 36a of the stabilization portion 36. By pressing the stabilization portion 36 toward the skin until the contact surface 37a of this guide portion 37 makes contact with the skin, it is possible to secure a force with which the stabilization portion 36 and the needle tube 5 are pressed toward the skin in a range of a predetermined value or more. Thus, the portion of the needle tube 5 which protrudes from the needle protrusion surface 22a (portion corresponding to protrusion length L) will be stuck into the skin reliably.

The distance (This will hereinafter be referred to as "guide-portion height".) Y from the contact surface 37a of the guide portion 37 to the end surface 36a of the stabilization portion 36 is set such that the needle tube 5 and the stabilization portion 36 can be pressed toward the skin and stick it with an appropriate pressure. Thus, the pressure exerted on the skin by the needle tube 5 and the stabilization portion 36 is guided by the guide portion 37 and it is possible for the user to get a feeling of security.

In a case in which the inner diameter d of the stabilization portion 36 is in the range of 11 mm to 14 mm, the guide-portion height Y is appropriately determined based on the length (This will hereinafter be referred to as "guide-portion length".) X from the distal end surface of the guide portion 37 to the outer peripheral surface of the stabilization portion 36. For example, when the inner diameter d of the stabilization portion 36 is 12 mm and the guide-portion length X is 3.0 mm, the guide-portion height Y is set in the range of 2.3 mm to 6.6 mm.

The fitting portion 32 of the second member 12 includes a tube hole 32a which has a size corresponding to that of the discharge portion 62 of the syringe 3. This hole 32a has an inner diameter which continuously decreases toward the side of the insertion portion 31. An inner surface of the fitting portion 32 forming the cylindrical hole 32a is provided with a screw groove 38 for screw engagement with the discharge portion 62 of the syringe 3.

Also, at the fitting portion 32, there is provided an engagement portion 39 for engagement with the communication member 13. This engagement portion 39 is formed as a stepped portion projecting radially inward from an inner surface of the fitting portion 32, and has engaging surfaces 39a and 39b approximately orthogonal to the axial direction of the second member 32. The engaging surface 39a of the engagement portion 39 is engaged with a flange portion 42, described later, of the communication member 13 and the engaging surface 39b is engaged with a discharge portion 62 of the syringe 3.

Next, there will be explained the communication member 13. The communication member 13 is composed of an elastically deformable material. For the material of the communication member 13, there can be cited various kinds of rubber materials such as natural rubber, silicone rubber and the like, various thermoplastic elastomers based on polyurethane, styrene and the like, or elastic materials formed by the mixtures of the above materials.

The communication member 13 is engaged with the engagement portion 39 of the second member 12 and is interposed between the first member 11 and the syringe 3. Then, the space occurring between the outer circumferential surface on the proximal end 5B side of the needle tube 5 protruded from the first member 11 and the second member 12 is buried. This communication member 13 includes a main body portion 41 and a flange portion 42 provided at one end in the axial direction of this main body portion 41.

The body portion 41 is formed in an approximately cylindrical shape, and has end surfaces 41a, 41b perpendicular to the axial direction of the body portion 41. The locking member 14 abuts the end surface 41a of the body portion 41, and the distal end of the discharge portion 62 provided at the syringe 3 abuts the end surface 41b of the body portion 41. In other words, the end surface 41b constitutes an abutting surface on which the distal end of the discharge portion 62 is to abut.

The body portion 41 is provided with an insertion hole 45 through which the proximal end 5B side of the needle tube 5 protruding from the end surface 21b of the first member 11 is to be inserted. This insertion hole 45 extends in the axial direction of the body portion 41 and is opened at the end surfaces 41a and 41b. The inner surface of the body portion 41 which forms the insertion hole 45 is formed by an end surface side spaced portion 46, an abutting surface side spaced portion 47, and a close contact portion 48.

The end surface side spaced portion 46 is formed with an opening of the insertion hole 45 at the end surface 41a. This end surface side spaced portion 46 is radially apart from the outer peripheral surface of the needle tube 5 and is formed in a tapered shape such that the diameter of the insertion hole 45 increases toward the end surface 41a. Thus, it is possible for the proximal end 5B side of the needle tube 5 protruding from the end surface 21b of first member 11 to be inserted easily into the insertion hole 45. Note that the shape of the end surface side spaced portion 46 of the insertion hole 45 is not limited to the tapered shape insofar as it is a shape by which it is easy for the needle tube 5 to pass through the insertion hole 45.

The abutting surface side spaced portion 47 is formed with an opening of the insertion hole 45 on the end surface (abutting surface) 41b. This abutting surface side spaced portion 47 is apart from the outer peripheral surface of the needle tube 5 and is formed in a tapered shape such that the diameter of the insertion hole 45 is continuously increased toward the end surface 41b. By providing the abutting surface side spaced portion 47 at the communication member 13, even if the end surface 41b side of the main body portion 41 is elastically deformed, it is possible to make it so as not to cover the opening of the proximal end 5B of the needle tube 5.

The close contact portion 48 is formed between the end surface side spaced portion 46 and the abutting surface side spaced portion 47. This close contact portion 48 makes liquid-tight close contact with the outer peripheral surface of the needle tube 5. Thus, it is possible to prevent the medicine inside the syringe 3 from penetrating between the needle tube 5 and the communication member 13 and from leaking to the first member 11 side of the first member.

The flange portion 42 is formed in a ring-shape which projects radially outward from the outer peripheral surface of the body portion 41. A flat surface on one side of the flange portion 42 forms the same flat surface as the end surface 41a of the body portion 41 and the locking member 14 abuts thereto. A flat surface on the other side of the flange portion 42 abuts the engaging surface 39a of the engagement portion 39 provided on the second member 12. In other words, the communication member 13 is attached to the second member 12 by sandwiching the flange portion 42 between the engagement portion 39 of the second member 12 and the locking member 14.

Next, there will be explained the locking member 14. The locking member 14 is a member showing one embodiment of an engagement portion provided at the insertion portion 31 of the second member 12. This locking member 14 is formed in a plate shape and includes an engagement surface 14a with which the other end of the pressing force restricting member 15 is engaged and an abutting surface 14b which abuts the communication member 13. On the abutting surface 14b of the locking member 14, there is provided an engagement protrusion 51 which engages with a mounting groove 31b provided at the insertion portion 31 of the second member 12. By a mechanism in which this engagement protrusion 51 is engaged with the mounting groove 31b of the insertion portion 31, the locking member 14 is fixed at the insertion portion 31.

Also, the locking member 14 is provided with a through hole 52 through which the proximal end 5B side of the needle tube 5 protruded from the end surface 21b of the first member 11 passes. This through hole 52 is opened on the engagement surface 14a and the abutting surface 14b, and it is formed in such a taper shape whose diameter becomes continuously larger toward the engagement surface 14a.

For the material of the locking member 14, it is allowed, similarly as the second member 12, to apply synthetic resins such as polycarbonate, polypropylene, polyethylene and the like and besides, it is allowed to apply a metal such as stainless, aluminum or the like.

Next, there will be explained the pressing force restricting member 15. The pressing force restricting member 15 is arranged between the first member 11 and the second member 12. Note that the locking member 14 intervenes between the pressing force restricting member 15 and the second member 12. This pressing force restricting member 15 is a compressed coil spring and restricts pushing force (pressing force) added to the skin through the first member 11. In other words, it restricts the pressing force to the skin by the needle tip 5A of the needle tube 5 and the needle protrusion surface 22a.

One end of the pressing force restricting member 15 is engaged with the second engagement portion 24 provided in the first member 11 and the other end thereof is engaged with the engagement surface 14a of the locking member 14. This pressing force restricting member 15 is contracted by being elastically deformed when the pressing force added from the first member 11 to the skin exceeds an appropriate pressing force. Thus, it is possible to prevent the skin abutting the needle protrusion surface 22a from expanding and becoming thin, and it is possible to reliably position the needle tip 5A (bevel 5a) of the needle tube 5 at the upper layer region of the skin. Note that the appropriate pushing force (pressing force) by the needle protrusion surface 22a is in the range of 3 to 20.

In this exemplified embodiment, the pressing force restricting member 15 is formed as a compressed coil spring. However, for the pressing force restricting member relating to the present invention, it is enough if there is employed an elastic member which deforms elastically when a predetermined pressing force is added and it is also possible, for example, to apply other spring members such as a flat spring and the like and to apply a sponge, a gel or a rubber member.

Next, there will be explained the cap 8. The cap 8 is formed in a tubular shape with a bottom and is detachably fitted to the guide portion 37 of the second member 12. This cap 8 covers the whole needle hub 6 to which the needle tube 5 is fixed (see FIG. 5A). As for the injection needle assembly 2 before attached to the syringe 3, an opening portion of the cap 8 is sealed by a sealing film 55, thereby keeping the needle hub 6 and the needle tube 5 in an aseptic condition.

Also, by a mechanism in which the cap 8 covers the needle tip 5A of the needle tube 5, it is possible to prevent the needle tip 5A from touching a user's finger or the like at the time of mounting the injection needle assembly 2 to the syringe 3. Further, by attaching the cap 8 to the used needle hub 6, it is possible to keep the injection needle assembly 2 always in a safe state. As a result thereof, it is possible for the user to carry out a disposal-treatment of the used injection needle assembly 2 or the like without anxiety.

[Syringe]

Next, there will be explained the syringe 3 with which the injection needle assembly 2 is connected detachably. The syringe includes a syringe body 61 and a discharge portion 62 continuous with this syringe body 61. The syringe body 61 is composed of a circular cylinder body. The discharge portion 62 projects from one end in the axial direction of the syringe body 61 and is composed of a circular cylinder body having an outside diameter smaller than that of the syringe body 61.

The discharge portion 62 is formed in a tapered shape such that the outer diameter is continuously decreased toward the distal direction. An end surface 62a (see FIG. 4) constituting the distal end of the discharge portion 62 is a flat surface orthogonal to the axial direction and abuts the end surface (abutting surface) 41h of the communication member 13. Also, the outer peripheral surface of the discharge portion 62 is provided with the screw portion 63 for screw engagement with the second member 12.

A gasket (not shown) is housed in the syringe body 61. An internal space of the syringe body 61 is partitioned by the gasket and a space on one side which communicates with the discharge portion 62 forms a liquid chamber 66 together with the space inside the discharge portion 62. In the other space inside the syringe body 61, a plunger (not shown) is disposed. The plunger is connected to the gasket and protruded from an opening at the other end of the syringe body 61. By operating this plunger, the gasket is moved in the axial direction within the syringe body 61, whereby suction of the medicine into the liquid chamber 66 and discharge of the medicine filling the liquid chamber 66 are carried out.

It is possible for the materials of the syringe body 61 and the discharge portion 62 to use synthetic resins such as polycarbonate, polypropylene, polyethylene or the like and besides, it is also allowed to use glasses and the like.

[Assembling Method for Medicine Injection Apparatus]

Next, there will be explained an assembling method of the medicine injection needle assembly 1 with reference to FIG. 5.

Figure 5A:
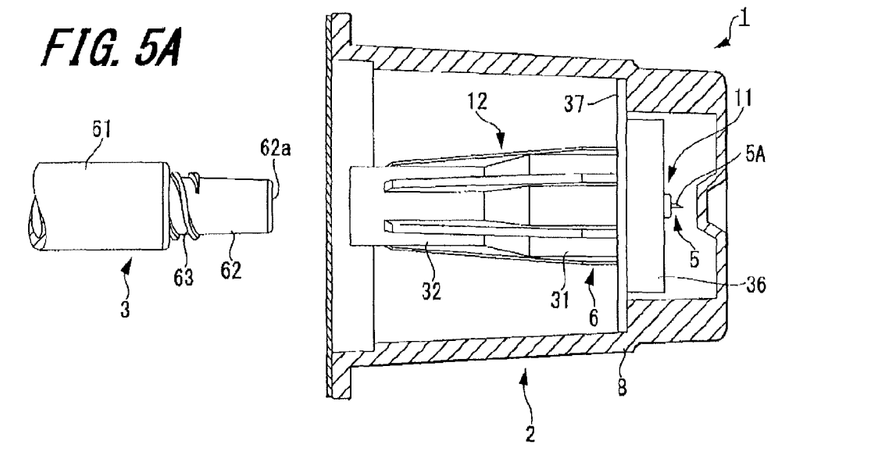
FIG. 5A is an explanatory view showing a state before an injection needle assembly relating to the first exemplified embodiment of the medicine injection apparatus of the present invention is mounted on the syringe.

FIG. 5A is an explanatory view showing the injection needle assembly 2 before being attached to the syringe 3. FIG. 5B is an explanatory view showing a state in which the sealing film 55 is removed and the syringe 3 is attached to the injection needle assembly 2. FIG. 5C is an explanatory view showing a state in which the cap is removed from the medicine injection needle assembly 1.

The medicine injection apparatus 1 is assembled by mounting the injection needle assembly 2 to the syringe 3. As shown in FIG. 5A, for the injection needle assembly 2 before being attached to the syringe 3, a sealing film 55 is mounted on the cap 8, and the needle hub 6 and the needle tube 5 are kept in an aseptic condition. In order to mount the injection needle assembly 2 to the syringe 3, first, the sealing film 55 is removed from the cap 8. Thus, the opening portion of the cap 8 is opened and the second member 12 of the needle hub 6 facing the opening portion thereof is exposed.

Figure 5B:
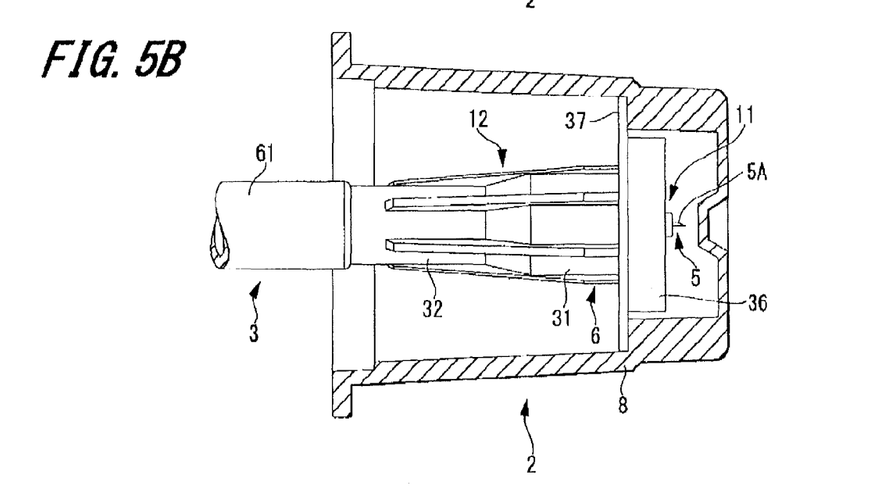
FIG. 5B is an explanatory view showing a state in which a sealing film is removed and the syringe is attached to the injection needle assembly.
Figure 5C:
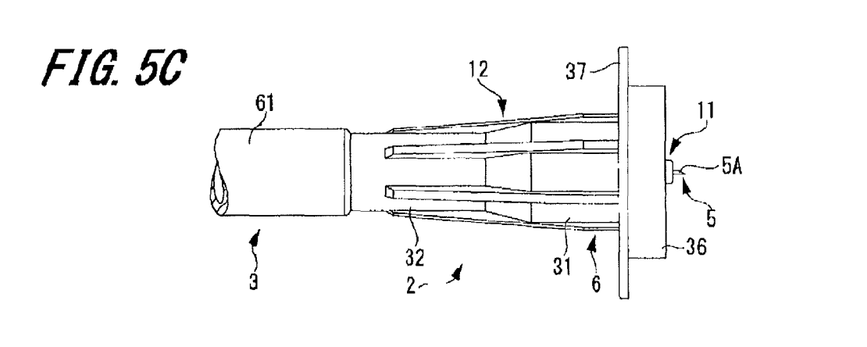
FIG. 5C is an explanatory view showing a state in which a cap is removed.

Next, as shown in FIG. 5B, the discharge portion 62 of the syringe 3 is inserted into the fitting portion 32 of the second member 12. Then, the screw portion 63 provided on the discharge portion 62 is screwed into the screw groove 38 (see FIG. 4) of the fitting portion 32. At that time, the cap 8 covers the needle tip 5A of the needle tube 5, so that it is possible to prevent the needle point 5A from touching a user's finger or the like. When the screw portion 63 of the discharge portion 62 is threadedly engaged with the screw groove 38 of the fitting portion 32, the mounting of the injection needle assembly 2 to the syringe 3 is completed.

In a state of attaching the injection needle assembly 2 to the syringe 3, the end surface 62a constituting the distal end of the discharge portion 62 is perpendicularly brought into abutment on the end surface (abutting surface) 41b of the communication member 13 provided in the injection needle assembly 2, and presses that end surface 41b (see FIG. 3). Thus, the end surface 62a of the discharge portion 62 and the end surface 41b of the communication member 13 come into liquid-tight close contact with each other, and the needle hole of the needle tube 5 and the liquid chamber 66 of the syringe 3 communicate with each other. As a result thereof, it is possible to prevent the medicine filled in the liquid chamber 66 of the syringe 3 from leaking out inside the needle hub 6 of the injection needle assembly 2 and it is possible to eject a predetermined quantity of medicine from the needle tip 5A of the needle tube 5.

Also, since the end surface 62a of the discharge portion 62 is perpendicularly brought into abutment on the end surface 41b of the communication member 13 so as to bring both of them into liquid-tight close contact with each other, there is no need for precise adjustment of the position of the needle tube 5 with respect to the needle hub 6 of the injection needle assembly 2. Therefore, it is possible to simplify the assembling work of the needle hub 6 and the needle tube 5 and it is possible to improve the production efficiency.

Also, by installing the abutting surface side spaced portion 47 on the communication member 13, there is little or no possibility that the end surface 41b of the communication member 13 pressed by the end surface 62a of the discharge portion 62 might be elastically deformed so as to enter into the discharge portion 62. As a result thereof, it is possible to make a situation in which the needle hole on the proximal end 5B side in the needle tube 5 is prevented from being occluded by the communication member 13.

Thereafter, as shown in FIG. 50, the cap 8 is removed from the guide portion 37 of the needle hub 6. Thus, the medicine injection needle assembly 1 becomes in a state of being usable.

[Method of Using Medicine Injection Apparatus]

Next, there will be explained a method of using the medicine injection apparatus 1 with reference to FIG. 3. In order to stick the needle tip 5A of the needle tube 5 into a living body, first, the end surface 36a of the stabilization portion 36 is faced to the skin. Thus, the needle tip 5A of the needle tube 5 is made to face the skin to be stuck. Next, the medicine injection apparatus 1 is moved approximately perpendicularly with respect to the skin, the needle tip 5A is stuck into the skin and concurrently, the end surface 36a of the stabilization portion 36 is pressed toward the skin. At that time, the needle protrusion surface 22a contacts the skin, whereby it is possible to deform the skin flatly and it is possible to stick the needle tip 5A side of the needle tube 5 into the skin as much as the protrusion length L.

Next, the end surface 36a of the stabilization portion 36 is pressed until the contact surface 37a of the guide portion 37 comes into contact with the skin. Here, the guide-portion height Y is set to be the length by which the stabilization portion 36 is pressed to the skin by a proper pressing force. Therefore, the pressure which presses the skin becomes a predetermined value depending on the stabilization portion 36. Also, when the pressing force added to the skin from the needle protrusion surface 22a of the first member 11 exceeds the proper pressing force, the pressing force restricting member 15 is deformed elastically and is contracted. Thus, it is possible to prevent the skin abutting the needle protrusion surface 22a from becoming thin by being expanded. As a result thereof, it is possible to make the needle tip 5A (bevel 5a) of the needle tube 5 positioned at the upper layer region of the skin reliably.

In the medicine injection apparatus in the past, the thickness of the upper layer region of the skin at the deltoid periphery is small and when the needle protrusion surface 22a is pressed down to the skin by a strong pressing force exceeding 20N, it sometimes happened that the needle tube reached the subcutaneous region or a water blister was not formed, and there was a case in which it was not possible to inject the medicine into the skin upper layer region. However, for the medicine injection apparatus 1, even if the needle protrusion surface 22a is pressed down to the skin by such a strong pressing force exceeding 20N, the first member and the needle tube 5 are moved toward the syringe 3 side, so that the needle tip 5A of the needle tube 5 (bevel 5a) is positioned at the skin upper layer region and it is possible to inject the medicine into the skin upper layer region.

Further, by a mechanism that the stabilization portion 36 abuts the skin, the posture of the medicine injection apparatus 1 is stabilized and it is possible to stick the needle tube 5 with respect to the skin in a straight manner. Also, it is possible to prevent a shaking of the needle tube 5, which occurs after the sticking, so that it is possible to carry out stable administration of the medicine. In case of a needle tube having an extremely small protrusion length of, for example, approximately 0.5 mm, it sometimes happens that the needle tip may not stick into the skin even if the needle tip is brought into abutment with the skin. However, caused by a mechanism in which the skin pressed by the stabilization portion 36 is pressed down perpendicularly, the skin on the inner side of the stabilization portion 36 is pulled and it becomes a state in which tension is applied to the skin. Therefore, it becomes difficult for the skin to escape with respect to the needle tip 5A of the needle tube 5. Accordingly, by providing the stabilization portion 36, there can be also obtained such an effect that the needle tip 5A is stuck into the skin more easily.

After sticking the needle point 5A side of the needle tube into the skin, the plunger (not shown) is pushed and the gasket (not shown) is moved toward the discharge part 62 side. Thus, the medicine filling the liquid chamber 66 of the syringe 3 is pushed out from the discharge part 62, passes through the needle hole of the needle tube 5, and is injected via the needle point 5A into the skin upper layer region.

In this exemplified embodiment, there is employed such a constitution in which the stabilization portion 36 and the guide portion 37 are provided at the second member 12 of the needle hub 6. However, for the medicine injection apparatus relating to the present invention, it is also possible to employ such a constitution in which the stabilization portion and the guide portion are provided at the syringe 3.

Also, in this exemplified embodiment, the discharge portion 62 of the syringe 3 is made so as to be screwed to the fitting portion 32 of the needle hub 6. However, for the medicine injection apparatus relating to the present invention, it is also allowed to connect the discharge portion 62 to the fitting portion 32 only by the fitting itself. In that case, such as this exemplified embodiment, it is recommended that the discharge portion 62 is formed in such a taper shape in which the diameter thereof becomes continuously smaller toward the distal end thereof. As a result thereof, even if fluctuations in manufacturing occur in the sizes of the discharge portion 62 and the fitting portion 32, it is possible to closely-contact the end surface 62a of the discharge portion 62 and the end surface 41b of the communication member 13 in a liquid tight manner.

Also, in this exemplified embodiment, there is employed such a constitution in which the other end of the pressing force restricting member 15 is made to engage with (abut) the engagement surface 14a of the locking member 14. In other words, the pressing force restricting member 15 is engaged with the second member 12 through the locking member 14. However, regarding the injection needle assembly and the medicine injection apparatus of the present invention, it is also possible to employ such a constitution in which the pressing force restricting member directly engages with the second member. In that case, it is enough if an engagement portion, with which the pressing force restricting member engages, is provided on the second member.

2. Second Exemplified Embodiment

Medicine Injection Apparatus

Next, there will be explained a second exemplified embodiment of the medicine injection apparatus of the present invention with reference to FIG. 6.

Figure 6:
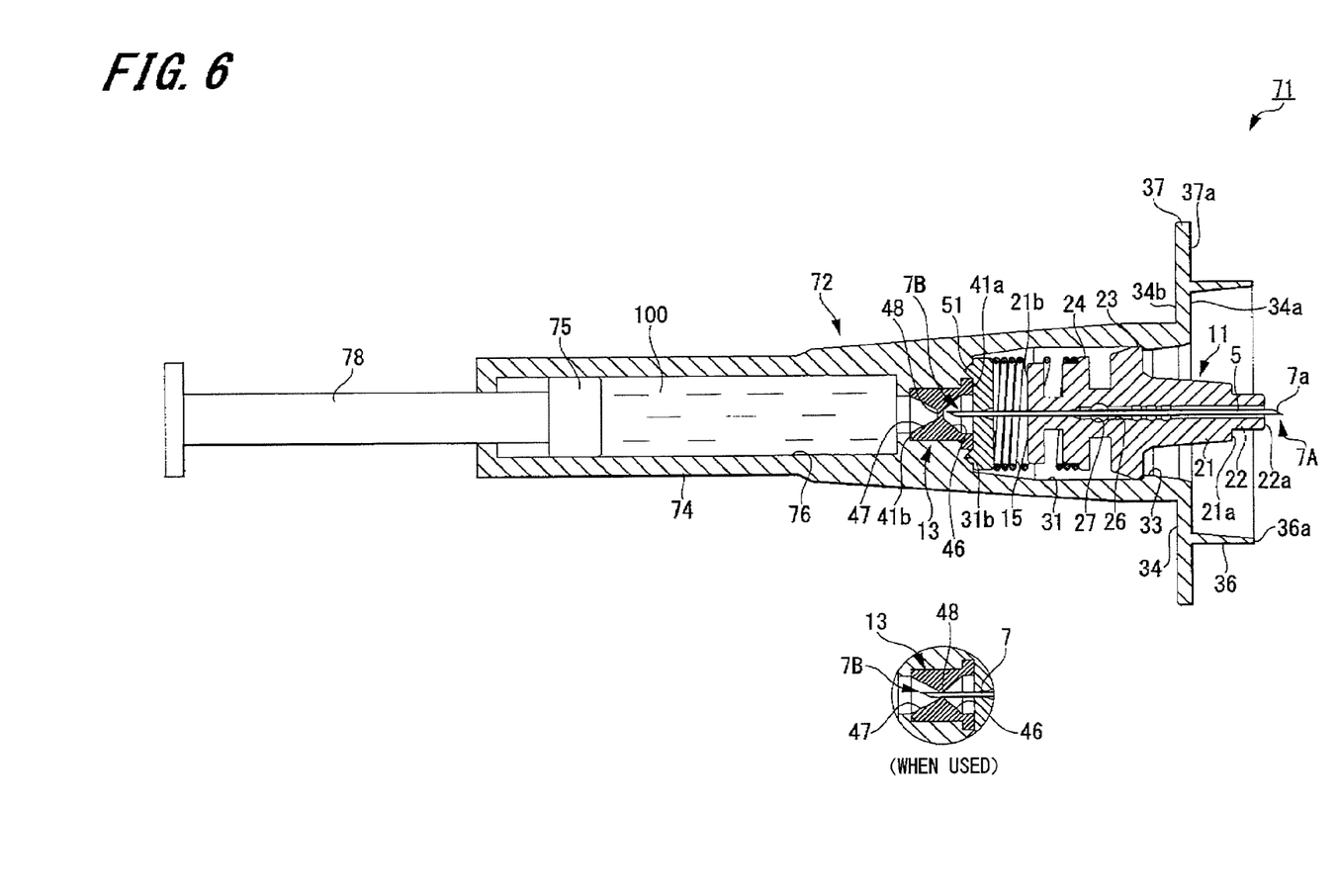
FIG. 6 is a cross-sectional view of a second exemplified embodiment of the medicine injection apparatus of the present invention.

FIG. 6 is a cross-sectional view of a second exemplified embodiment of the medicine injection apparatus.

As shown in FIG. 6, a medicine injection apparatus 71 of the second exemplified embodiment includes constitutions similar to those of the medicine injection apparatus 1 of the first exemplified embodiment. An aspect in which this medicine injection apparatus 71 is different from the medicine injection apparatus 1 lies in that there is provided with a housing portion 74 in which a medicinal solution 100 is housed in a second member 72. In other words, the second member 72 of the medicine injection apparatus 71 constitutes to be a prefilled syringe filled with the medicinal solution 100 beforehand. Therefore, there will be explained the second member 72 here, and the repetitive explanation will be omitted by applying the same reference numerals to the portions in common with those of the medicine injection apparatus 1.

The second member 72 of the medicine injection apparatus 71 is formed approximately in a tubular shape.
One end portion in the axial direction of this second member 72 forms the insertion portion 31 into which the base portion 21 of the first member 11 is to be inserted and the other end portion thereof forms the housing portion 74 which houses the medicinal solution 100. One end of the housing portion 74 communicates with the insertion hole 45 of the communication member 13 and concurrently, communicates with the needle hole of the needle tube 5, and the other end thereof is opened.

A gasket (sealing member) 75 for sealing the housing portion 74 in a liquid tight manner is housed in the housing portion 74. In other words, the gasket 75 partitions the housing portion 74 into two spaces and one space communicating with the communication member 13 forms a liquid chamber 76. Also, in the other space in the housing portion 74, a plunger (press member) 78 is disposed. This plunger 78 is connected to the gasket 75 and protrudes from an opening at the other end of the housing portion 74. By operating this plunger, the gasket 75 is moved in the axial direction within the housing portion 74, whereby discharge of the medicine filling the liquid chamber 76 is carried out.

Also, the needle tube 7 of the medicine injection apparatus 71 is constituted to be a double-head needle and includes a first needle tip 7A which is stuck into the living body and a second needle tip 7B which is inserted into the communication member 13. Before using the medicine injection apparatus 71, the second needle tip 7B of the needle tube 7 is arranged at the end surface side separated portion 46 of the communication member 13 and does not pass through the close-contact portion 48. Therefore, the needle hole of the needle tube 7 does not communicate with the liquid chamber 76 and it never happens that the medicinal solution 100 enters into the needle hole of the needle tube 7. Thus, it is possible to maintain the sterilization property of the liquid chamber 76.

On the other hand, at the time of the use of the medicine injection apparatus 71, the needle tube 7 moves to the housing portion 74 side together with the first member 11 by a mechanism in which the needle protrusion surface 22a of the first member 11 is pressed toward the skin. Thus, the second needle tip 7B of the needle tube 7 passes through the close-contact portion 48 of the communication member 13 and is positioned at the contact surface side separated portion 47, and the needle hole of the needle tube 7 and the liquid chamber 76 communicate with each other. Then, when the plunger 78 is pressed, the medicinal solution 100 is injected from the first needle tip 7A to the skin upper layer region by passing through the needle hole of the needle tube 7.

Even in the medicine injection apparatus 71 constituted like that, when the pressing force added onto the skin from the needle protrusion surface 22a of the first member 11 exceeds an appropriate pressing force, the pressing force restricting member 15 is deformed elastically and is contracted. Thus, it is possible to prevent the skin abutting the needle protrusion surface 22a from becoming thin by being expanded. As a result thereof, it is possible to position the first needle tip 7A (bevel 7a) of the needle tube 7 at the skin upper layer region reliably.

As described above, there were explained exemplified embodiments of the medicine injection apparatus and the injection needle assembly of the present invention together with the operational effects thereof. However, the injection needle assembly and the medicine injection apparatus of the present invention are not to be limited by the exemplified embodiments mentioned above and it is possible to employ various kinds of modified practices within the scope without departing from the gist of the invention described in the claims.

In the first to third exemplified embodiments mentioned above, there was employed a constitution in which the adjustment portion is provided at the first member. However, it is also possible for the adjustment portion relating to the present invention to be provided as a member separated from the first member. In such a case, for example, the adjustment portion is fixed on the peripheral surface of the needle tube.

DESCRIPTION OF REFERENCE NUMERALS 1, 71: medicine injection apparatus; 2: injection needle assembly; 3: syringe; 5: needle tube; 5A: needle tip; 5B: proximal end; 6: needle hub; 8: cap; 11: first member; 12, 72: second member; 13: communication member; 14: locking member (locking portion); 15: pressing force restricting member; 21: base portion; 22: adjustment portion; 22a: needle protrusion surface; 23: first engagement portion; 24: second engagement portion; 26: through hole; 27: hole for injection; 31: insertion portion; 32: fitting portion; 33: stopper portion; 34: connection piece; 36: stabilization portion; 36a: end surface; 37: guide portion; 37a: contact surface; 38: screw groove; 39: engagement portion; 41: main body portion; 42: flange portion; 45: insertion hole; 46: end surface side separated portion; 47: contact surface side separated portion; 48: close-contact portion; 51: engagement protrusion; 52: through hole; 55: sealing film; 61: syringe main body; 62: discharge portion; 63: screw portion; 66, 76: liquid chamber; 74: housing portion; 75: gasket (sealing member); 78: plunger; 100: medicinal solution

The invention claimed is:
1. An injection needle assembly, comprising:
a needle tube having a needle tip to be stuck into a skin;
a first member holding the needle tube so that the first member and the needle tube move together;
a second member which holds the first member movably in an axial direction of the needle tube and concurrently, into which a discharge portion of a syringe is fitted;
an adjustment portion which is provided at a periphery of the needle tube and which is formed with a needle protrusion surface which abuts the skin in case of sticking the needle tube into a living body;
a pressing force restricting member which is arranged between the first member and the second member and which restricts pressing force added from the first member to the skin;
a stabilization portion protruding from the second member and configured such that when the needle tube is stuck into the skin and the second member is advanced toward the skin, the needle protrusion surface contacts the skin first, and then the stabilization portion contacts the skin after the needle protrusion surface has contacted the skin;
wherein the second member includes an insertion portion for inserting the first member; and
the pressing force restricting member is engaged with a first engagement portion provided on an outer circumferential surface of the first member and with a second engagement portion provided at the insertion portion of the second member.
2. The injection needle assembly according to claim 1, wherein the pressing force restricting member is composed of an elastic member which deforms elastically when a predetermined pressing force is added to the first member.

3. The injection needle assembly according to claim 1, wherein the pressing force restricting member restricts the pressing force to 10N or less.

4. A medicine injection apparatus, comprising:
a syringe including a discharge portion;
a needle tube having a needle tip to be stuck into a skin;
a first member holding the needle tube so that the first member and the needle tube move together;
a second member which holds the first member movably in an axial direction of the needle tube and concurrently, into which the discharge portion of the syringe is fitted;
an adjustment portion which is provided at a periphery of the needle tube and which is formed with a needle protrusion surface which abuts the skin in case of sticking the needle tube into a living body;
a pressing force restricting member which is arranged between the first member and the second member and which restricts pressing force added from the first member to the skin;
a stabilization portion protruding from the second member and configured such that when the needle tube is stuck into the skin and the second member is advanced toward the skin, the needle protrusion surface contacts the skin first, and then the stabilization portion contacts the skin after the needle protrusion surface has contacted the skin;
wherein the second member includes an insertion portion for inserting the first member; and
the pressing force restricting member is engaged with a first engagement portion provided on an outer circumferential surface of the first member and with a second engagement portion provided at the insertion portion of the second member.

5. A medicine injection apparatus, comprising:
a needle tube having a needle tip to be stuck into a skin;
a first member holding the needle tube so that the first member and the needle tube move together;
a second member which holds the first member movably in an axial direction of the needle tube and which includes a housing portion with a medicinal solution housed therein, a sealing member for sealing the housing portion in a liquid tight manner, and a press member connected to the sealing member;
an adjustment portion which is provided at a periphery of the needle tube and which is formed with a needle protrusion surface which abuts the skin in case of sticking the needle tube into a living body;
a pressing force restricting member which is arranged between the first member and the second member and which restricts pressing force added from the first member and to the skin;
a stabilization portion protruding from the second member and configured such that when the needle tube is stuck into the skin and the second member is advanced toward the skin, the needle protrusion surface contacts the skin first, and then the stabilization portion contacts the skin after the needle protrusion surface has contacted the skin;
wherein the second member includes an insertion portion for inserting the first member; and
the pressing force restricting member is engaged with a first engagement portion provided on an outer circumferential surface of the first member and with a second engagement portion provided at the insertion portion of the second member.

6. The injection needle assembly according to claim 1, wherein the stabilization portion protrudes from the second member in the axial direction of the needle tube.

7. The injection needle assembly according to claim 1, wherein the stabilization portion possesses a tubular shape.

8. The injection needle assembly according to claim 1, wherein an end surface of the stabilization portion that contacts the skin is circular in shape.

9. The injection needle assembly according to claim 1, wherein the second member includes a hole in which is positioned the first member, and the stabilization portion is located radially outwardly of the hole.

10. The medicine injection apparatus according to claim 4, wherein the stabilization portion protrudes from the second member in the axial direction of the needle tube.

11. The medicine injection apparatus according to claim 4, wherein the stabilization portion possesses a tubular shape.

12. The medicine injection apparatus according to claim 4, wherein an end surface of the stabilization portion that contacts the skin is circular in shape.

13. The medicine injection apparatus according to claim 4, wherein the second member includes a hole in which is positioned the first member, and the stabilization portion is located radially outwardly of the hole.

14. The medicine injection apparatus according to claim 5, wherein the stabilization portion protrudes from the second member in the axial direction of the needle tube.

15. The medicine injection apparatus according to claim 5, wherein the stabilization portion possesses a tubular shape.

16. The medicine injection apparatus according to claim 5, wherein an end surface of the stabilization portion that contacts the skin is circular in shape.

17. The medicine injection apparatus according to claim 5, wherein the second member includes a hole in which is positioned the first member, and the stabilization portion is located radially outwardly of the hole.

18. An injection needle assembly, comprising:
a needle tube having a needle tip to be stuck into a skin;
a first member holding the needle tube so that the first member and the needle tube move together;
a second member which holds the first member movably in an axial direction of the needle tube and concurrently, into which a discharge portion of a syringe is fitted;
an adjustment portion which is provided at a periphery of the needle tube and which is formed with a needle protrusion surface which abuts the skin in case of sticking the needle tube into a living body;
a pressing force restricting member which is arranged between the first member and the second member and which restricts pressing force added from the first member to the skin;
a stabilization portion protruding from the second member and configured such that when the needle tube is stuck into the skin and the second member is advanced toward the skin, the needle protrusion surface contacts the skin first, and then the stabilization portion contacts the skin after the needle protrusion surface has contacted the skin;
wherein there is included a communication member which is arranged inside the second member and which communicates a proximal side opposite to a needle tip side of the needle tube with the discharge portion of the syringe in a liquid tight manner.

19. A medicine injection apparatus, comprising:
a syringe including a discharge portion;
a needle tube having a needle tip to be stuck into a skin;

a first member holding the needle tube so that the first member and the needle tube move together;

a second member which holds the first member movably in an axial direction of the needle tube and concurrently, into which the discharge portion of the syringe is fitted;

an adjustment portion which is provided at a periphery of the needle tube and which is formed with a needle protrusion surface which abuts the skin in case of sticking the needle tube into a living body;

a pressing force restricting member which is arranged between the first member and the second member and which restricts pressing force added from the first member to the skin;

a stabilization portion protruding from the second member and configured such that when the needle tube is stuck into the skin and the second member is advanced toward the skin, the needle protrusion surface contacts the skin first, and then the stabilization portion contacts the skin after the needle protrusion surface has contacted the skin;

wherein there is included a communication member which is arranged inside the second member and which communicates a proximal side opposite to a needle tip side of the needle tube with the discharge portion of the syringe in a liquid tight manner.

20. A medicine injection apparatus, comprising:

a needle tube having a needle tip to be stuck into a skin;

a first member holding the needle tube so that the first member and the needle tube move together;

a second member which holds the first member movably in an axial direction of the needle tube and which includes a housing portion with a medicinal solution housed therein, a sealing member for sealing the housing portion in a liquid tight manner, and a press member connected to the sealing member;

an adjustment portion which is provided at a periphery of the needle tube and which is formed with a needle protrusion surface which abuts the skin in case of sticking the needle tube into a living body;

a pressing force restricting member which is arranged between the first member and the second member and which restricts pressing force added from the first member and to the skin;

a stabilization portion protruding from the second member and configured such that when the needle tube is stuck into the skin and the second member is advanced toward the skin, the needle protrusion surface contacts the skin first, and then the stabilization portion contacts the skin after the needle protrusion surface has contacted the skin;

wherein there is included a communication member which is arranged inside the second member and which communicates a proximal side opposite to a needle tip side of the needle tube with the discharge portion of the syringe in a liquid tight manner.

* * * * *